United States Patent
Khare (10) Patent No.: US 9,382,175 B2
(45) Date of Patent: Jul. 5, 2016

(54) PROCESSED SUPPORT AND METHODS OF MAKING AND USING SAME

(71) Applicant: Chevron Phillips Chemical Company LP, The Woodlands, TX (US)

(72) Inventor: Gyanesh P. Khare, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 30 days.

(21) Appl. No.: 14/472,022

(22) Filed: Aug. 28, 2014

(65) Prior Publication Data

US 2014/0371500 A1    Dec. 18, 2014

Related U.S. Application Data

(62) Division of application No. 13/227,037, filed on Sep. 7, 2011, now Pat. No. 8,835,341.

(51) Int. Cl.
| | |
|---|---|
| *C07C 5/00* | (2006.01) |
| *C07C 5/41* | (2006.01) |
| *B01J 29/06* | (2006.01) |
| *C01B 39/32* | (2006.01) |
| *B01J 37/22* | (2006.01) |
| *B01J 29/068* | (2006.01) |
| *B01J 29/62* | (2006.01) |
| *C01B 39/02* | (2006.01) |
| *C10G 35/095* | (2006.01) |
| *B01J 29/60* | (2006.01) |

(52) U.S. Cl.
CPC .............. *C07C 5/412* (2013.01); *B01J 29/06* (2013.01); *B01J 29/068* (2013.01); *B01J 29/60* (2013.01); *B01J 29/62* (2013.01); *B01J 37/22* (2013.01); *C01B 39/026* (2013.01); *C01B 39/32* (2013.01); *C10G 35/095* (2013.01); *B01J 2229/34* (2013.01); *B01J 2229/38* (2013.01); *C07C 2529/06* (2013.01); *C07C 2529/08* (2013.01); *C07C 2529/40* (2013.01); *C07C 2529/60* (2013.01)

(58) Field of Classification Search
USPC .................................. 585/321, 322, 418, 419
See application file for complete search history.

(56) References Cited

U.S. PATENT DOCUMENTS

| | | | |
|---|---|---|---|
| 3,216,789 | A | 11/1965 | Breck et al. |
| 3,864,283 | A | 2/1975 | Schutt |
| 3,926,780 | A | 12/1975 | Ward |
| 3,945,943 | A | 3/1976 | Ward |
| 4,300,015 | A | 11/1981 | Kirsch et al. |
| 4,447,316 | A | 5/1984 | Buss |
| 4,987,109 | A | 1/1991 | Kao et al. |
| 4,994,250 | A | 2/1991 | Occelli |
| 5,169,813 | A | 12/1992 | Miller et al. |
| 5,514,362 | A | 5/1996 | Miller |
| 5,558,851 | A | 9/1996 | Miller |
| 6,190,539 | B1 | 2/2001 | Holtermann et al. |
| 6,207,042 | B1 | 3/2001 | Holtermann et al. |
| 6,495,723 | B1 | 12/2002 | DeVera et al. |
| 6,812,180 | B2 | 11/2004 | Fukunaga |
| 7,153,801 | B2 | 12/2006 | Wu |
| 8,835,341 | B2 | 9/2014 | Khare |
| 2004/0259719 | A1 | 12/2004 | Wu |

OTHER PUBLICATIONS

Dai, Lian-Xin, et al., "Effect of KCI Addition Method on the Pt/KL Catalyst for the Aromatization of Hexane," Journal of Catalysis, vol. 147, pp. 311-321, 1994, Academic Press, Inc.
Fukunaga, Tetsuya, et al., "Halogen-promoted Pt/KL Zeolite Catalyst for the Production of Aromatic Hydrocarbons from Light Naphtha," Catal. Surv. Asia, vol. 14, pp. 96-102, 2010, Springer.
Sugimoto, Michio, et al., "Improvement of platinum-supported zeolite catalysts for n-hexane aromatization by halocarbon treatment and alkaline soaking," Applied Catalysis A: General, vol. 96, pp. 201-216, 1993, Elsevier Science Publishers B.V., Amsterdam.

*Primary Examiner* — Elizabeth Wood
(74) *Attorney, Agent, or Firm* — Conley Rose, P.C.; Rodney B. Carroll; Monte R. Rhodes (57) ABSTRACT

A method for removing tightly bound sodium from a zeolitic support comprising contacting the support with a sodium specific removal agent to produce a treated support. A method comprising providing an aromatization catalyst comprising a treated support, and contacting the aromatization catalyst with a hydrocarbon feed in a reaction zone under conditions suitable for the production of an aromatic product. A catalyst support comprising an L-zeolite having less than 0.35 wt. % sodium.

18 Claims, 1 Drawing Sheet

PROCESSED SUPPORT AND METHODS OF MAKING AND USING SAME

CROSS-REFERENCE TO RELATED APPLICATIONS

This application is a divisional of and claims priority to U.S. patent application Ser. No. 13/227,037 filed on Sep. 7, 2011, published as US 2013/0060072 A1, now U.S. Pat. No. 8,835,341, entitled "Processed Support and Methods of Making and Using Same," which application is incorporated by reference herein in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

1. Technical Field

The present disclosure relates to catalyst compositions. More specifically, the present disclosure relates to improved aromatization catalyst compositions and methods of producing same.

2. Background

Large pore zeolite catalysts are useful to dehydrocyclize aliphatic hydrocarbons to produce aromatic hydrocarbons. For example, large pore zeolite catalysts are useful for reforming light petroleum naphtha (e.g., $C_6$-$C_8$) to benzene, toluene and xylenes. Examples of such aromatization catalysts include silica bound large pore zeolite supports containing platinum and halides such as chloride and fluoride. Due to the commercial importance of such catalysts, an ongoing need exists for improved aromatization catalysts and methods of making and using same.

SUMMARY

Disclosed herein is a method for removing tightly bound sodium from a zeolitic support comprising contacting the support with a sodium specific removal agent to produce a treated support.

Also disclosed herein is a method comprising providing an aromatization catalyst comprising a treated support, and contacting the aromatization catalyst with a hydrocarbon feed in a reaction zone under conditions suitable for the production of an aromatic product.

Further disclosed herein is a catalyst support comprising an L-zeolite having less than 0.35 wt. % sodium.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Disclosed herein are low sodium content aromatization catalysts and methods of making and using same. Herein, a low sodium content refers to a sodium content of equal to or less than about 0.35 wt. % based on the total weight of the catalyst support (e.g., weight of the catalyst support prior to metal impregnation) alternatively from about 0.001 wt. % to about 0.35 wt. %, alternatively from about 0.01 wt. % to about 0.30 wt. %, alternatively from about 0.10 wt. % to about 0.25 wt. %, or alternatively from about 0.15 wt. % to about 0.20 wt. %.

The catalysts disclosed herein may be used in reforming processes such as for example, the conversion of hydrocarbons to aromatics, and are hereinafter referred to as aromatization catalysts. An aromatization catalyst of the type disclosed herein may display a number of desirable properties such as for example, a reduced temperature at start of reaction ($T_{SOR}$), higher catalytic activity, and/or a lower fouling rate when compared to an otherwise similar aromatization catalyst having a higher sodium content.

In an embodiment, the aromatization catalyst comprises a support, wherein the support comprises one or more zeolites. The term "zeolite" generally refers to hydrated, crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms is typically equal to 2. The framework exhibits a negative electrovalence that typically is balanced by the inclusion of cations such as metals, alkali metals, alkaline earth metals, or hydrogen. Thus, zeolites are a group of natural or synthetic hydrated aluminosilicate minerals that contain alkali and alkaline metals. Zeolites are characterized by a framework structure that encloses interconnected cavities occupied by any suitable ion-exchangeable large metal cations such as potassium or barium and water molecules permitting reversible dehydration. The actual formula of the zeolite may vary without changing the crystalline structure. In an embodiment, the molar ratio of silicon to aluminum (Si/Al) in the zeolite may vary from about 1.0 to about 3.5.

In an embodiment, the support comprises a large-pore zeolite. The term "large-pore zeolite" as used herein refers to a zeolite having an effective pore diameter of from about 5 Angstroms (Å) to about 15 Å, alternatively from about 6 Å to about 9 Å. Large pore crystalline zeolites suitable for use in this disclosure include without limitation L-zeolite, X-zeolite, Y-zeolite, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, ZZA-26, SSZ-31, SSZ-33, SSZ-35, SSZ-37, SSZ-41, SSZ-42, SSZ-44, MCM-58, mordenite, faujasite, or combinations thereof. In an embodiment, the large pore zeolite has an isotypic framework structure.

In an embodiment, the support comprises an L-zeolite. L-type zeolites are a sub-group of zeolites. The designations LTL zeolite or Linde type L zeolite also refer to this same sub-group of zeolitic materials. Typical L-type zeolites contain mole ratios of oxides in accordance with the following formula:

wherein "M" designates at least one exchangeable cation such as barium, calcium, cerium, lithium, magnesium, potassium, sodium, strontium, and zinc as well as non-metallic cations like hydronium and ammonium ions which may be replaced by other exchangeable cations without causing a substantial alteration of the basic crystal structure of the L-type zeolite. The "n" in the formula represents the valence of "M", "x" is 2 or greater; and "y" is the number of water molecules contained in the channels or interconnected voids with the zeolite. L-zeolite, its X-ray diffraction pattern, its properties, and methods for its preparation are described in detail in U.S. Pat. No. 3,216,789, the content of which is hereby incorporated by reference. In an embodiment, the catalyst support comprises L-zeolite wherein M is potassium, also referred to as K/L-zeolite. In another embodiment, the catalyst support comprises L-zeolite wherein M is barium, also referred to as Ba/L-zeolite.

The support may further comprise a material which functions to bind together the zeolitic material. This material, termed a binder, may comprise silica, alumina, alternatively a low acidity silica or a low acidity alumina. In an embodiment, the silica comprises particles having a diameter of from about 2 nm to about 25 nm, alternatively from about 5 nm to about 20 nm, alternatively from about 7 nm to about 12 nm. In an embodiment, the silica particles may be in the form of a silica sol. A silica sol may be obtained by dispersing the silica particles in water. The silica sol may be provided in about 20 to about 30 vol. % aqueous solution having a pH of from about 9.0 to about 10.5 with a viscosity of equal to or less than about 20 mPa·s at 25° C., alternatively from about 1 to about 20 mPa·s at 25° C. An example of a silica sol suitable for use in this disclosure includes without limitation SNOWTEX® UP or SNOWTEX® ST which are colloidal silica sols comprising silica particles that are commercially available from Nissan Chemical Industries Ltd. The binder may additionally comprise alumina; clays such as montmorillonite and kaolin; the refractory oxides of metals of Groups IVA and IVB of the Periodic Table of the Elements; oxides of silicon, titanium, zirconium or combinations thereof; or combinations thereof.

In an embodiment, the silica bound zeolite support may be prepared by forming a mixture comprising a zeolite, a binder, water, and optional extrusion aids which may then be shaped. The mixture may be formed into any suitable shape, for example via extrusion. The mixture may contain from about 50 wt. % to about 95 wt. % zeolite, alternatively from about 75 wt. % to about 90 wt. % zeolite, or alternatively from about 80 wt. % to about 90 wt. % zeolite. The mixture may contain from about 5 wt. % to about 50 wt. % binder, alternatively from about 10 wt. % to about 25 wt. % binder, or alternatively from about 10 wt. % to about 20 wt. % binder. The mixture may contain zeolite and a binder combined in a weight ratio of from about 1:99 to about 99:1, alternatively from about 90:10 to about 85:15, or alternatively from about 92:8 to about 82:18. In an embodiment, the aqueous volume percent of the mixture formed by combining the zeolite and binder (e.g., silica) may be from about 20% to about 60%, alternatively from about 25% to about 55%, alternatively from about 30% to about 45%. In an embodiment, the mixture will contain sufficient water to retain a desired shape. Water may be added separately to the mixture or as a solution of one or more other components, for example silica sol. The amount of water may be varied and selected according to one of ordinary skill in the art with the aid of this disclosure. In an embodiment, the mixture is extruded and may contain up to about 50 grams of water per about 100 grams of green extrudate where green extrudate refers to the shaped mixture exiting a die.

In an embodiment, the mixture comprises L-zeolite bound with silica, alternatively L-zeolite bound with colloidal silica, alternatively KL-zeolite bound with silica, or alternatively KL-zeolite bound with colloidal silica.

In an embodiment, the mixture comprising a binder, a zeolite, and water is formed into shaped particles. In an embodiment, the mixture may be formed into any suitable shape. Methods for shaping particles are well known in the art, and include, for example, extrusion, spray drying, pelletizing, agglomerization and the like. In an embodiment, the mixture is formed into a green extrudate, for example as described in U.S. Pat. Nos. 5,558,851 and 5,514,362, each of which are incorporated herein in their entirety. In an embodiment, the mixture further comprises an extrusion aid. An extrusion aid may function to improve the rheology of the mixture. This improvement in the rheology of the mixture may function to improve flow of the mixture through the extrusion die. Improved flow through the extrusion die leads to easier equipment start-up, smoother extrusion, faster processing, lower extrusion pressures, and improved product appearance. In an embodiment, the extrusion aid comprises cellulose derivatives, ethylene glycol, stearic acid or combinations thereof. In an embodiment, the extrusion aid comprises cellulose ether such as methylcellulose, carboxymethylcellulose, ethylhydroxyethylcellulose, hydroxyethylcellulose, hydroxypropylcellulose, methylhydroxyethylcellulose, methylhydroxypropylcellulose, or combinations thereof. An example of an extrusion aid suitable for use in this disclosure includes without limitation METHOCEL®, a cellulose based material commercially available from Dow Chemical Company. Extrusion aids, their effective amounts and methods of incorporation into the mixture may be varied and selected according to ordinary skill in the art with the aid of this disclosure.

Excess water from the green extrudate may be removed by drying to form a dried green extrudate prior to further processing. Conventional methods for drying wet solids can be used to dry the green extrudate, and may include, for example drying in air or an inert gas such as nitrogen or helium. The air or inert gas may be circulating, moving, or static. Drying temperatures may range from about 175° F. to about 400° F., alternatively from about 200° F. to about 300° F., or alternatively from about 225° F. to about 275° F. Drying times may range from equal to or greater than about 1 hour, alternatively from about 1 hour to about 10 hours, or alternatively from about 2 hours to about 5 hours.

In an embodiment, the dried green extrudate may be calcined to form a calcined extruded base hereinafter termed the "support." Calcination temperatures may range from about 500° F. to about 1500° F., alternatively from about 700° F. to about 1100° F., or alternatively from about 850° F. to about 1100° F. Calcination times may range from about 0.5 to about 5 hours, alternatively from about 0.5 to about 1.5 hours. In such embodiments, the calcination may be carried out in an oxygen containing atmosphere having an air flow of from about 10 to about 20 cubic feet per hour (CFH), alternatively the calcination may be carried out in air at an air flow of from about 10 to about 20 CFH, alternatively, the calcination may be carried out in "dry" air having an air flow of about 10 to about 20 CFH. As used herein "dry" air refers to air having a dew point of less than about −40° F. The support is a silica bound zeolite support and may be directly used in a catalyst preparation, see below, or may be further processed according to the following description.

The thus prepared support generally contains two different types of sodium; "readily removable" sodium which can be removed by washing the support with water at a suitable temperature, (e.g., from about 50° F. to about 120° F.) while the other type of sodium, "tightly bound" sodium, cannot be easily removed without utilizing drastic conditions (e.g., temperatures greater than about 180° F. and/or a pH of less than about 3). Herein, "tightly bound" refers to sodium that is associated with the support but is presumably deeply embedded into the structure of the support. Use of drastic conditions to remove the tightly bound sodium would adversely affect the catalyst's performance. In the instant application, a processed support and a method for making the processed support is disclosed which further reduces the concentration of "tightly bound" sodium in the support by contacting the support with a sodium-specific removal agent. In the instant application, a method is provided for the removal of these tightly-bound sodium atoms without compromising (i.e., destabilizing, degrading) the components of the processed support. In one embodiment, the support is contacted with a sodium-specific removal agent and then optionally contacted with a wash solution, in another embodiment. The wash solution may optionally contain an alkali metal compound. In either embodiment, the processed support has a reduced amount of tightly bound sodium when compared to supports prepared in the absence of (i) a sodium-specific removal agent or (ii) a sodium-specific removal agent followed by washing.

In an embodiment, the support is contacted with a sodium-specific removal agent. The sodium-specific removal agent may be any material which can reduce the amount of "tightly bound" sodium present in the support. Alternatively, the sodium-specific removal agent comprises an ammonium-containing compound, alternatively an alkyl, aryl or arylalkyl ammonium-containing compound, alternatively an alkyl, aryl or arylalkyl ammonium hydroxide. Examples of sodium-specific removal agents suitable for use in this disclosure include without limitation tetraethyl ammonium hydroxide, tetramethyl ammonium hydroxide (TMAOH), tetrapropyl ammonium hydroxide, tetraisopropyl ammonium hydroxide, tetrabutyl ammonium hydroxide, tetraisobutyl ammonium hydroxide, or combinations thereof. In an embodiment, the support is contacted with the ammonium-containing compound to reduce the amount of "tightly bound" sodium present in the support.

The sodium-specific removal agent may be prepared by dissolving and/or suspending a sodium-specific removal agent in an appropriate solvent. Examples of solvents suitable for use in this disclosure include without limitation water, alcohol, or any other solvent in which the sodium-specific removal agent is soluble or combinations thereof. The sodium-specific removal agent solution may be prepared to have a pH ranging from about 7 to about 14, alternatively from about 8 to about 13, or alternatively from about 10 to about 12. The sodium-specific removal agent concentration in the treating solution may vary from about 0.01 wt. % to about 10 wt. %, alternatively from about 0.1 wt. % to about 5 wt. %, or alternatively from about 0.5 wt. % to about 2.0 wt. % based on the total weight of treating solution. The sodium-specific removal agent may be contacted with the support for a time period of from about 0.1 hour to about 24 hours, alternatively from about 0.2 hours to about 3 hours, or alternatively from about 0.3 hours to about 1 hour at a temperature ranging from about 60° F. to about 200° F., alternatively from about 80° F. to about 140° F., or alternatively from about 90° F. to about 110° F. The support having been contacted with the sodium-specific removal agent is termed a treated support.

In some embodiments, the sodium-specific removal agent may be removed and the treated support contacted with an additional amount of sodium-specific removal agent such that the support undergoes a plurality of sodium-specific removal agent contact steps/sequences. In one embodiment, a treated support may be formed via a plurality of sodium-specific removal agent contact steps/sequences.

In an embodiment, the treated support may be washed by contacting the treated support with a wash solution to form a treated and washed support. The wash solution may be any solution that when contacted with the treated support may reduce the amount of "readily removable" alkali metal present. In an embodiment, the wash solution comprises any fluid compatible with the treated support such as for example water, methanol, ethanol, propanol, isopropanol or combinations thereof. In another embodiment, the wash solution may contain an alkali metal salt, alternatively a potassium-containing salt such as potassium hydroxide, potassium acetate, potassium bromide, potassium hydroxide, potassium fluoride, potassium iodide, potassium t-butoxide, potassium ethoxide, or combinations thereof. The term washing, as used herein, is meant to include any process whereby liquid (e.g., water) in excess of the material's pore volume is contacted with the support. The "readily removable" alkali is defined herein as the alkali that can be washed out of the support after 1, 2, 3, 4, or 5 washings (using a 1:1 volume of liquid to wt of support) at ambient temperature. In an embodiment, the wash solution is distilled or deionized water having a pH of from about 5 to about 9. The washing temperature may range from about 70° F. to about 200° F., alternatively of from about 80° F. to about 130° F., or alternatively from about 90° F. to about 110° F. The washing time may range from about 5 to about 60 minutes per wash, alternatively from about 15 to about 30 minutes per wash. Hereinafter, the washing temperatures and times are collectively termed the "wash conditions."

In an embodiment, the support may be first washed by contacting the support with a wash solution under wash conditions to form a washed support, and then treated by contacting the washed support with a sodium-specific removal agent to form a washed and treated support. In some embodiments the washed and treated support can then be again washed with a wash solution under wash conditions. In yet another embodiment, the treated support may be washed with a wash solution under wash conditions and then treated again. In any of these embodiments, the resultant support (e.g., washed and then treated support; washed; then treated and then washed again; or treated, then washed, then treated again) is termed a processed support.

The treated or processed support may be dried at atmospheric or other pressure to form a processed dried support. The drying temperature may range from about 175° F. to about 400° F., alternatively from about 200° F. to about 300° F., or alternatively from about 225° F. to about 275° F. The drying time may be at least about 1 hour, alternatively from about 1 to about 10 hours, or alternatively from about 2 to about 5 hours.

The treated or processed dried support may be recalcined to form a processed, calcined dried support. The calcining temperature may range from about 500° F. to about 1200° F., alternatively from about 700° F. to about 1100° F., or alternatively from about 850° F. to about 1000° F. The calcining time may range from about 0.5 hours to about 5.0 hours, alternatively from about 0.5 hours to about 1.5 hours. In such embodiments, the calcination may be carried out in an oxygen-containing atmosphere having an air flow of from about 10 CFH to about 20 CFH, alternatively the calcination may be carried out in air at a flow of from about 10 CFH to about 20 CFH, alternatively, the calcination may be carried out in "dry" air having an air flow of about 10 CFH to about 20 CFH. The calcined dried support is a silica bound zeolite support and may be directly used in a catalyst preparation. Hereinafter, the calcined dried support, made from a dried support that was treated or processed is referred to as the catalyst support.

In an embodiment, a method of preparing an aromatization catalyst comprises contacting the catalyst support with one or more catalytic compounds.

The catalyst support may be impregnated with one or more Group VIII metals to form a metalized support. As will be understood by one of ordinary skill in the art, in handling of a support of the type described herein, precautions are typically employed to ensure that sodium is not reintroduced to the essentially sodium free support during any subsequent processing of the material such as during metals or any promoter loading. The metal may be added to the support by employing a variety of known and conventional techniques, e.g., ion-exchange, incipient wetness, pore fill, impregnation, etc. In an embodiment, the metal is added to the support by impregnation with a metal-containing solution. The metal in the metal-containing solution may be at least one Group VIII metal; alternatively, Pt, Pd, Rh, Ir, Ru, Os, or combinations thereof; alternatively, platinum. In an embodiment, the metal comprises platinum that is added to the support via contact with a metal-containing solution containing at least one platinum-containing compound. Examples of platinum-containing compounds suitable for contact with the catalyst support include without limitation platinum compounds that form positively charged platinum complex ions in solution such as for example platinum salts such as chlorides and nitrates; platinum complexes with amines; or combinations thereof. For example, the platinum-containing compound can be any platinum-containing compound including, but not limited to, ammonium tetrachloroplatinate, chloroplatinic acid, diamineplatinum (II) nitrite, bis-(ethylenediamine)platinum (II) chloride, platinum (II) acetylacetonate, dichlorodiamine platinum, platinum (II) chloride, tetraamineplatinum (II) hydroxide, tetraamineplatinum chloride, tetraamineplatinum (II) nitrate, or combinations thereof. In an embodiment, the platinum source is tetraamine platinum chloride (TAPC). The amount of platinum in the metalized support may range from about 0.1 wt. % to about 5 wt. %, alternatively from about 0.1 wt. % to about 3 wt. %, or alternatively from about 0.3 wt. % to about 1.8 wt. %.

In an embodiment, at least one halide is added to the catalyst support by contact with a halide-containing compound to form a halided support. In another embodiment, two or more halides are added to the support by contact with two or more halide-containing compounds to form a halided catalyst support. The halides may be added to the catalyst support separately; alternatively, the halides may be added to the catalyst support at the same time. Such halides may be incorporated during the previously described metallization to produce a metalized halided catalyst support, alternatively the halides may be incorporated during a separate step that may be pre- or post addition of the metal, to form a metalized halided catalyst support. Examples of suitable halides include without limitation fluoride, chloride, bromide, iodide, or combinations thereof. Such halides may be introduced as an ammonium halide compound. The ammonium halide compound may comprise one or more compounds represented by the formula $N(R)_4X$, where X is a halide and where R represents a hydrogen or a substituted or unsubstituted carbon chain molecule having 1-20 carbons wherein each R may be the same or different. In an embodiment, R is selected from the group consisting of methyl, ethyl, propyl, butyl, and combinations thereof, alternatively methyl. Examples of suitable ammonium compounds represented by the formula $N(R)_4X$ include ammonium chloride, ammonium fluoride, and tetraalkylammonium halides such as tetramethylammonium chloride (TMAC), tetramethylammonium fluoride (TMAF), tetraethylammonium chloride, tetraethylammonium fluoride, tetrapropylammonium chloride, tetrapropylammonium fluoride, tetrabutylammonium chloride, tetrabutylammonium fluoride, methyltriethylammonium chloride, methyltriethylammonium fluoride, or combinations thereof. In an embodiment, the halided catalyst support comprises silica bound zeolite and further comprises chloride present in an amount of from about 0.1 wt. % to about 5 wt. %, alternatively from about 0.1 wt. % to about 3 wt. %, or alternatively from about 0.3 wt. % to about 1.8 wt. %. In an embodiment, the halided catalyst support comprises silica bound zeolite and further comprises fluoride present in an amount of from about 0.1 wt. % to about 5 wt. %, alternatively from about 0.1 wt. % to about 3 wt. %, or alternatively from about 0.3 wt. % to about 1.8 wt. %. In an embodiment, the halided catalyst support comprises both chloride and fluoride, which may be present in a Cl:F ratio of from about 1:10 to about 10:1, alternatively from about 1:5 to about 5:1, alternatively from about 1:2 to about 2:1. Once the catalyst support has been contacted with halogens and metal it is hereinafter referred to as a metalized halided support. In an embodiment, the metalized halided support is allowed to set for several hours prior to additional processing. In an embodiment, the metalized halided support is allowed to set for about 1 to about 24 hours, alternatively for about 2 to about 8 hours, alternatively for about 3 to about 6 hours.

Following the preparation of the metalized halided support by contact with a metal and one or more halides, the metalized halided support may then be further processed as described herein. The metalized halided support may be processed to remove undesirable compounds remaining from the contacting steps, for example by drying to remove compounds and/or heating to decompose compounds. In an embodiment, the metalized halided support is dried and calcined as described previously herein.

The metalized halided support may be dried to form a dried metalized halided support, which is an aromatization catalyst. The drying temperature may range from about 100° F. to about 300° F., alternatively from about 150° F. to about 250° F., alternatively from about 200° F. to about 220° F. The drying time may range from about 0.1 to about 6 hours, alternatively from about 0.2 to about 4 hours, alternatively from about 0.2 to about 3 hours. The drying may be carried out at ambient pressures or under a vacuum, alternatively under a vacuum from about 10 to about 40 inches of mercury. The metalized halided support may be dried using any equipment known to one of ordinary skill in the art for drying under the disclosed conditions. For example, the metalized halided support may be dried using a standard rotary evaporator operating at a temperature of greater than about 100° F. and under a vacuum of about 20 to about 30 inches of mercury.

The dried metalized halided support may be calcined to form a dried and calcined metalized halided support which may be employed as an aromatization catalyst. The calcining temperature may range from about 400° F. to about 900° F., alternatively from about 500° F. to about 700° F., alternatively from about 550° F. to about 600° F. The calcining time may range from about 0.5 hours to about 5 hours, alternatively from about 0.5 hours to about 2.5 hours. The calcination may be carried out in an oxygen-containing atmosphere under a gas flow rate of from about 5 CFH to about 20 CFH. Alternatively, the calcination may be carried out in air using a flow rate of from about 5 CFH to about 20 CFH, alternatively in dry air using a flow rate of about 5 CFH to about 20 CFH. Upon completion of processing the dried metalized halided support, alternatively the calcined metalized halided support, alternatively the dried and calcined metalized halided support is an aromatization catalyst which may be employed as an aromatization catalyst in a suitable chemical reaction and process.

In an embodiment, the aromatization catalyst prepared as disclosed herein is used as an aromatization catalyst in an aromatization reactor system comprising at least one aromatization reactor and its corresponding processing equipment. In an embodiment, the aromatization catalyst is used as an aromatization catalyst in an aromatization reactor system and is contacted with a hydrocarbon feed under conditions suitable for the conversion of at least a portion of the feed to aromatics. As used herein, the terms "aromatization," "aromatizing" and "reforming" refer to the treatment of a hydrocarbon feed to provide an aromatics enriched product, which in one embodiment is a product whose aromatics content is greater than that of the feed. Typically, one or more components of the feed undergo one or more reforming reactions to produce aromatics. Some of the hydrocarbon reactions that occur during the aromatization operation include the dehydrogenation of cyclohexanes to aromatics, dehydroisomerization of alkylcyclopentanes to aromatics, dehydrocyclization of acyclic hydrocarbons to aromatics, or combinations thereof. A number of other reactions also occur, including the dealkylation of alkylbenzenes, isomerization of paraffins, hydrocracking reactions that produce light gaseous hydrocarbons, e.g., methane, ethane, propane and butane, or combinations thereof.

The aromatization reaction occurs under process conditions that thermodynamically favor the dehydrocyclization reaction and limit undesirable hydrocracking reactions. The pressures may be from about 0 pounds per square inch gauge (psig) to about 500 psig, alternatively from about 25 psig to about 300 psig, alternatively from about 30 psig to about 70 psig. The molar ratio of hydrogen to hydrocarbons may be from about 0.1:1 to about 20:1, alternatively from about 0.5:1 to about 6:1, alternatively from about 1:1 to about 4:1. The operating temperatures include reactor inlet temperatures from about 700° F. to about 1050° F., alternatively from about 900° F. to about 1025° F. Finally, the liquid hourly space velocity for the hydrocarbon feed over the aromatization catalyst may be from about 0.1 $hr^{-4}$ to about 10 $hr^{-4}$, alternatively from about 0.5 $hr^{-4}$ to about 2.5 $hr^{-4}$.

The composition of the feed is a consideration when designing catalytic aromatization systems. In an embodiment, the hydrocarbon feed comprises non-aromatic hydrocarbons containing at least six carbon atoms. The feed to the aromatization system is a mixture of hydrocarbons comprising $C_6$ to $C_8$ hydrocarbons containing up to about 10 wt. % and alternatively up to about 15 wt. % of $C_5$ and lighter hydrocarbons ($C_5^-$) and containing up to about 10 wt. % of $C_9$ and heavier hydrocarbons ($C_9^+$). Such low levels of $C_9^+$ and $C_5^-$ hydrocarbons maximize the yield of high value aromatics. In some embodiments, an optimal hydrocarbon feed maximizes the percentage of $C_6$ hydrocarbons. Such a feed can be achieved by separating a hydrocarbon feedstock such as a full range naphtha into a light hydrocarbon feed fraction and a heavy hydrocarbon feed fraction, and using the light fraction.

In another embodiment, the feed is a naphtha feed. The naphtha feed may be a light hydrocarbon, with a boiling range of about 70° F. to about 450° F. The naphtha feed may contain aliphatic, naphthenic, or paraffinic hydrocarbons. These aliphatic and naphthenic hydrocarbons are converted, at least in part, to aromatics in the aromatization reactor system. While catalytic aromatization typically refers to the conversion of naphtha, other feedstocks can be treated as well to provide an aromatics-enriched product. Therefore, while the conversion of naphtha is one embodiment, the present disclosure can be useful for activating catalysts for the conversion or aromatization of a variety of feedstocks such as saturated hydrocarbons, paraffinic hydrocarbons, olefinic hydrocarbons, acetylenic hydrocarbons, cyclic paraffin hydrocarbons, cyclic olefin hydrocarbons, and mixtures thereof, alternatively saturated hydrocarbons.

The feedstock may be substantially free of sulfur, nitrogen, metals, and other known poisons for aromatization catalysts. In an embodiment, the feedstock contains less than about 100 ppb of sulfur. If present, such poisons can be removed using suitable methods. In some embodiments, the feed can be purified by first using conventional hydrofining techniques, then using sorbents to remove the remaining poisons. Such hydrofining techniques and sorbents are included in the purification process described below.

In an embodiment, the aromatization catalyst may be used for the production of an aromatic product which may then be recovered from the reaction zone and processed subsequently to produce benzene, toluene, paraxylene, orthoxylene, metaxylene or combinations thereof. For example, the aromatization catalyst may be used in a process comprising aromatizing a wide boiling range naphtha in a reformer, for example, a continuous catalytic reformer or semi-regenerative reformer, followed by distillation of the reformer effluent into an aromatics fraction. The aromatics fraction may comprise benzene, toluene, paraxylene, orthoxylene, metaxylene, or combinations thereof.

The xylene isomers orthoxylene, metaxylene, and paraxylene, are important chemical intermediates. Orthoxylene may be oxidized to make phthalic anhydride, which is used to make phthalate-based plasticizers among other things. Metaxylene may be oxidized to make isophthalic acid, which is used in unsaturated polyester resins. Paraxylene may be oxidized to make terephthalic acid, which in turn is used to make polymers such as polytrimethyleneterephthalate, polybutyleneterephthalate (PBT), and polyethyleneterephthalate (PET). PET is one of the largest volume polymers in the world and is used to make PET plastics (e.g., two liter PET bottles). It is also used to make polyester fiber, which in turn is used to make clothes and other fabrics In an embodiment, the aromatization catalyst may be used in the production of benzene which may be hydrogenated to form a hydrogenation product such as for example cyclohexane. For example, the benzene may be hydrogenated in a process involving a high-purity benzene feed and purified hydrogen. The conversion of benzene to cyclohexane is stoichiometric. A large portion of the cyclohexane production is used to produce intermediates for nylons such as for example nylon 6 and nylon 66. Nylon 6 is made by polymerizing caprolactam which is derived from the nitration of cyclohexane. Nylon 66 is made by polymerizing equal molar quantities of adipic acid and hexamethylene diamine (HMDA). Adipic acid is made by a two-step air and nitric acid oxidation of cyclohexane. The adipic acid is converted to HMDA by the reduction of adiponitrile (an intermediate). Adipic acid produced from cyclohexane is also used to manufacture esters for plasticizers and synthetic lubricants, as well as produce polyurethanes (synthetic leather).

In an embodiment, the aromatization catalyst functions to catalyze the production of benzene which may be further alkylated to produce ethylbenzene which is a raw material for the production of styrene. For example, benzene may be combined, typically in molar excess, with a suitable alkylating reagent having from 2 to 54 carbon atoms such as olefins (e.g., ethylene, propylene), halogenated alkanes, or mixtures thereof. In one embodiment at least a portion of the benzene may be alkylated with ethylene to produce ethylbenzene; which may be optionally followed by dehydrogenation of the ethylbenzene to styrene. In another embodiment at least a portion of the benzene may be alkylated with propylene to produce cumene.

An aromatization catalyst of the type described herein may display an improved catalytic performance when compared to an otherwise similar catalyst prepared in the absence of a sodium-specific removal agent. The improved catalytic performance may be measured by a variety of factors including without limitation reductions in the temperature start of run ($T_{SOR}$), increased catalyst lifetime, decreased catalyst fouling rate, selectivity for desired aromatic product, and the like. Additional measures of improved catalytic performance would be apparent to one of ordinary skill in the art.

In an embodiment, when used as catalysts in an aromatization reaction, the aromatization catalysts of this disclosure may display a reduced start of run temperature ($T_{SOR}$) when compared to an otherwise similar catalyst prepared in the absence of a sodium-specific removal agent. The $T_{SOR}$ may be experimentally estimated by determining the y-intercept of a linear regression fit to yield adjusted temperatures versus time and not including any initial low conversion catalyst break-in conditions or initial performance (i.e. from 15-40 hours in a 40-hour test). The aromatization catalysts of this disclosure may have a $T_{SOR}$ of from about 900° F. to about 950° F., alternatively of from about 910° F. to about 940° F., or alternatively of from about 915° F. to about 930° F. The $T_{SOR}$ of an aromatization catalyst of the type described herein may be decreased from about 5° F. to about 45° F., alternatively from about 10° F. to about 40° F., or alternatively from about 15° F. to about 25° F. when compared to an otherwise similar catalyst prepared in the absence of a sodium-specific removal agent. In general, the $T_{SOR}$ is inversely proportional to the catalyst activity such that the lower the $T_{SOR}$, the higher the catalyst activity.

In an embodiment, the aromatization catalysts of this disclosure may be further characterized by an increased useful catalyst lifetime when compared to an otherwise similar catalyst prepared in the absence of a sodium-specific removal agent. Herein, the useful catalyst lifetime refers to the time between when the catalyst is placed in service and when one or more parameters indicate that the catalyst should be removed from service (for example, reaching the end-of-run (EOR) temperature, reaching a temperature close to reactor metallurgical limits or if the operation is no longer economical). The aromatization catalysts may exhibit a useful catalyst lifetime that is increased by equal to or greater than about 30% when compared to an otherwise similar catalyst prepared in the absence of a sodium-specific removal agent, alternatively of from about 20% to about 25%, or alternatively from about 10% to about 20%.

In an embodiment, the aromatization catalysts of this disclosure may exhibit a reduced fouling rate when compared to an otherwise similar catalyst prepared in the absence of a sodium-specific removal agent. Herein, the fouling rate refers to the rate at which the catalyst decreases in activity due any number of reasons, for example nonselective poisoning by components present or formed in the reaction zone in which it is employed. Herein, a fouling rate is determined by establishing a temperature needed to achieve a targeted conversion of the feed to a selected wt. % aromatics in the $C_{5+}$ product. As the catalyst activity decreases due to fouling, the temperature may be increased to compensate for the loss of catalyst activity. The extent to which the temperature is adjusted over a specified time period to maintain the targeted activity is termed the fouling rate. The aromatization catalysts of this disclosure may have a fouling rate of from about 0.01° F./hour to about 0.5° F./hour, alternatively from about 0.05° F./hour to about 0.30° F./hour, or alternatively from about 0.1° F./hour to about 0.2° F./hour.

In an embodiment, the aromatization catalysts of this disclosure may produce a comparable amount of aromatics, also termed the aromatics levels, when compared to an otherwise similar catalyst prepared in the absence of a sodium-specific removal agent and reacted under similar conditions. The aromatics level may be expressed as the percentage of a given feed that is converted to $C_5$ or higher aromatics ($C_{5+}$). The aromatization catalysts may catalyze the conversion of from about 10% to about 90%, alternatively from about 30% to about 80%, or alternatively from about 60% to about 70% of a feed to $C_{5+}$ aromatics.

Without wishing to be limited by theory, the methodologies disclosed herein for the reduction of the sodium content in a catalyst system may be carried out without significant alterations in the catalyst acidity. Changes in the catalyst acidity may negatively impact catalyst performance as would be evidenced by increases in the $T_{SOR}$, increased fouling rates, decreased selectivity, and the like. In an embodiment, the aromatization catalysts of this disclosure display an acidity comparable to an otherwise similar catalyst prepared in the absence of a sodium-specific removal agent.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

Example 1

The effect of treating an aromatization catalyst with a sodium-specific removal agent was investigated. Four samples, designated Samples 1-4, were prepared in accordance with the procedures outlined herein. Sample 1, which was a control sample (i.e., untreated), comprised a fresh support used in the production of Aromax® Catalysts which were washed 3 times using deionized water heated to 120° F. Sample 2 was obtained by treating sample 1 with a 1 wt. % solution of TMAOH dissolved at a temperature of 100° F. for 0.33 hours. Samples 3 and 4 were obtained from sample 1 that had been subjected to 2 or 3 treatments respectively with TMAOH under the conditions described for Sample 2. All samples were dried at 250° F. for 4 hours, and then recalcined at 900° F. for an hour. Sodium content as determined by inductively coupled plasma analysis was performed on the samples to determine the sodium level and the results are tabulated in Table 1.

TABLE 1

| Sample | Treating | Sodium level, ppm | Sodium level, wt. % |
|---|---|---|---|
| 1 | None | 3984 | 0.3984 |
| 2 | 1x | 2411 | 0.2411 |
| 3 | 2x | 1656 | 0.1656 |
| 4 | 3x | 1757 | 0.1757 |

The results demonstrate that treating a bound KL-zeolite catalyst support with a sodium-specific removal agent (e.g., TMAOH) reduced the sodium level from 3984 ppm in the control sample, Sample 1, to 2411 ppm in a sample treated once, Sample 2. Additional treatments with the sodium-specific removal agent reduced the sodium level further as evinced by comparison of the control sample, Sample 1, which had a sodium level of 3984 ppm to that of a sample treated 3 times with the sodium specific removal agent, Sample 4, which had a sodium level of 1757 ppm.

Example 2

The $T_{SOR}$, fouling rate, and aromatic levels of an aromatization catalyst treated with a sodium specific removal agent were compared to those of an untreated catalyst. Catalyst A, which was a control sample (i.e., support was not treated with a sodium-specific removal agent), comprised a fresh Aromax® II Catalyst of the type commercially available from the Chevron Phillips Chemical Company LP of The Woodlands, Tex. Preparation of these catalysts is discussed in U.S. Pat. Nos. 6,812,180, 6,207,042, 6,190,539, and 7,153,801. For example, the catalyst may be prepared by impregnating a KL-zeolite-support with tetramethylammonium chloride (TMAC), and/or tetraethylammonium fluoride (TMAF), and tetraamineplatinum chloride (TAPC); and calcining the impregnated zeolite. Preparation of these catalysts is discussed in U.S. Pat. Nos. 6,812,180; 6,207,042; 6,190,539; and 7,153,801, each of which is incorporated by reference herein in its entirety.

Catalyst A contained an initial sodium level of 3785 ppm. Catalyst B was obtained by impregnating 80.17 g of Sample 2 with a mixture of 1.52 g of tetraamineplatinum (II) chloride (TAPC), about 1.42 g of ammonium fluoride (AF), about 0.64 g of ammonium chloride (AC) and about 38.48 g of water using incipient wetness techniques. The impregnated sodium-specific removal agent treated support was allowed to stand for about 4 hours at room temperature and then dried in a vacuum for about 3 hours at about 212° F. followed by a calcination at about 585° F. for 1 hour in flowing air. The resultant catalyst contained about 0.96 wt. % Pt, about 0.66 wt. % fluoride, and about 0.55 wt. % chloride as determined by standard analytical techniques.

Next, the catalytic performance of both catalyst A and catalyst B was investigated. Each sample was placed in a reactor comprising about a ¼ inch OD (6.4 mm) stainless steel reactor vessel in a temperature controlled furnace. The sample was dried and reduced under flowing hydrogen without recycle at a temperature from room temperature to about 900° F. for an hour. A feed stream of aliphatic hydrocarbons at a liquid hourly space velocity (LHSV) of about 12 hr$^{-1}$ and hydrogen at $H_2$:hydrocarbon mole ratio of about 1 was introduced to the reactor vessel at a feed rate of about 12 mL/min and a pressure of about 100 psig. The reactor effluent composition was regularly analyzed by gas chromatography to indicate the weight percentage of total aromatics in the $C_{5+}$ fraction. The reactor temperature was then adjusted to achieve the desired total wt. % aromatics in the $C_{5+}$ product, typically about 70 wt. %, and performance data was then collected. The tests were run for 40 hours in each case. The results are summarized in Table 2.

TABLE 2

| Sample | $T_{SOR}$, ° F. | Fouling Rate, ° F./hour | $C_{5+}$ Yield % |
|---|---|---|---|
| Catalyst A | 929 | 0.24 | 93.2 |
| Catalyst B | 916 | 0.08 | 92.4 |

The results demonstrate that Catalyst B which had been treated with the sodium-specific removal agent had a lower $T_{SOR}$ indicating higher activity and lower fouling rate than the untreated control, Catalyst A while displaying a comparable level of $C_{5+}$ yield in the product.

Example 3

As shown in Table 3, several catalysts were prepared using supports treated with sodium-specific removal agents (SSRA) and then washed with a wash solution at 100° F. for 0.33 hour after the sodium-specific removal agent treatment as described in Example 1 and indicated in Table 3. In some samples the wash solution contained a base. The catalyst preparation was conducted as described in Example 2. The details of treatment with the sodium-specific removal agent and washings are included in the Table. A support that had not been subjected to treatment with a sodium-specific removal agent but was washed three times with water was designated Sample 5 and was used to prepare catalysts C and D. A support which was neither treated with a sodium-specific removal agent nor washed with a solution was designated Sample 6 and was used to prepare catalysts E, F, and G.

TABLE 3

| Sample | SSRA Treatment (#treatments/ wt. % solution)[1] | Washing (#washes/ wt.% solution/)[1,2] | wt. % Na[3] | Catalyst Performance Test | | |
|---|---|---|---|---|---|---|
| | | | | $T_{SOR}$ ° F. | Fouling Rate °F./hr | $C_5^+$ Yield wt. % |
| Sample 5 | None | water (3/NA) | 0.40 | — | — | — |
| Catalyst A | None | water (3/NA) | 0.47 | 948 | 0.09 | 93.1 |
| Catalyst C | TMAOH (1/1.0%) | (before) water (3/NA) (after) KOH (3/0.28%) | 0.25 | 916 | 0.08 | 94.1 |
| Catalyst D | TMAOH (3/1.0%) | (before) water (3/NA) (after) KOH (3/0.56%) | 0.15 | 920 | 0.07 | 93.9 |
| Sample 6 | None | None | 0.55 | — | — | — |
| Catalyst E | TMAOH (1/0.5%) | (before) water (1/NA) (after) KOH (2/0.056%) | 0.32 | 919 | 0.17 | 93.6 |
| Catalyst F | TMAOH (1/0.5%) | (before) water (1/NA) (after) KNO3 (2/1.0%) | 0.19 | 930 | 0.10 | 94.1 |

TABLE 3-continued

| Sample | SSRA Treatment (#treatments/ wt. % solution)[1] | Washing (#washes/ wt.% solution/)[1,2] | wt. % Na[3] | Catalyst Performance Test | | |
|---|---|---|---|---|---|---|
| | | | | $T_{SOR}$ °F. | Fouling Rate °F./hr | $C_5^+$ Yield wt. % |
| Catalyst G | TMAOH (2/0.5%) | (before) water (1/NA) (after) KNO3 (2/1.0%) | 0.17 | 928 | 0.14 | 94.0 |

[1] All treatments and washes are conducted at 100° F. for 0.33 hr.
[2] (before) or (after) refers to the wash solution used and number of washes performed before or after the SSRA treatment, respectively.
[3] Determined by Inductively coupled plasma (ICP) analysis.
[4] NA means Not Applicable Catalysts C, D, E, and G had undergone sodium-specific removal agent treatment with tetramethyl ammonium hydroxide and in each case displayed a much lower $T_{SOR}$ temperature indicative of a higher initial catalyst activity as compared to Catalyst A which was not treated. Furthermore, the weight percent sodium in each treated sample as determined by inductively coupled plasma analysis displayed a reduced level of sodium as a result of treatment with a sodium-specific removal agent. The $C_{5+}$ yield of all treated samples was higher than the yield found for the untreated sample.

Example 4

Figure 1:
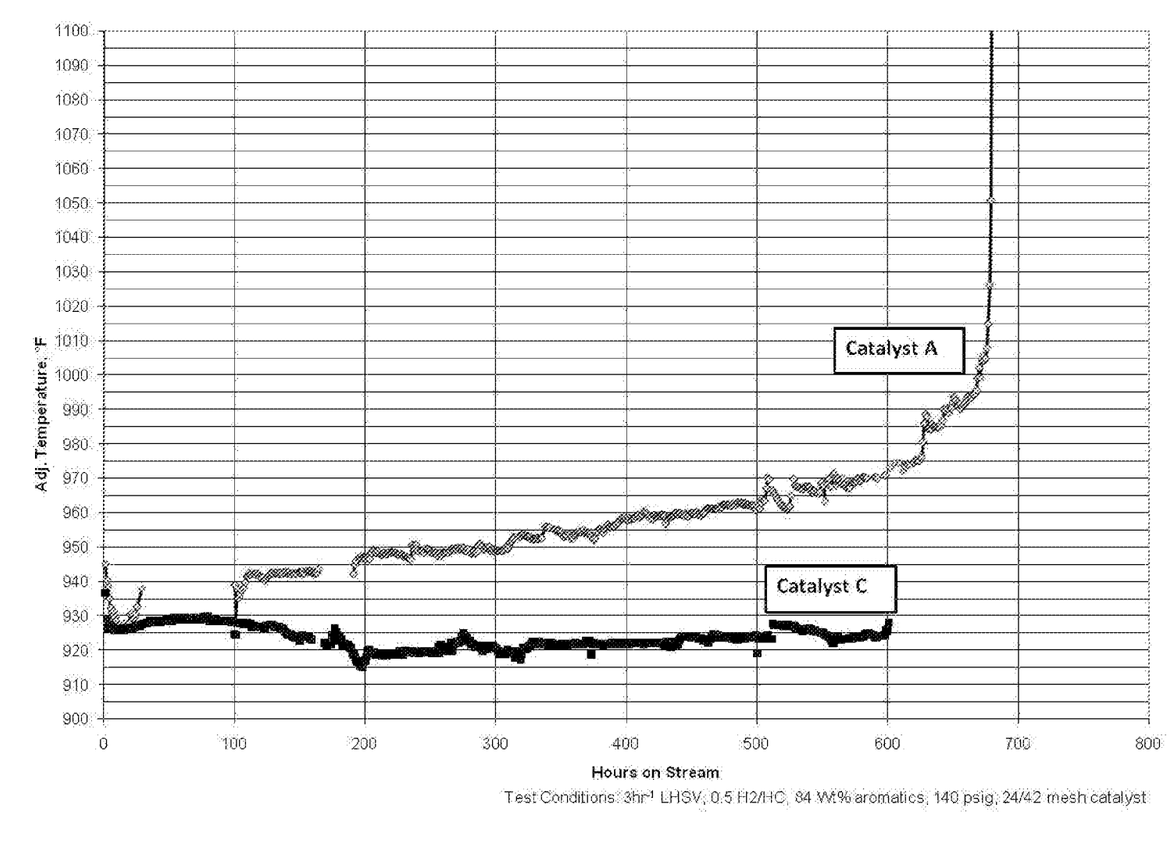
FIG. 1 is a plot of the adjusted temperature as a function of time on stream for the samples from example 4.

In order to measure the longer term activity performance and obtain an accurate assessment of the relative fouling rates, the sodium-specific removal agent treated Catalyst C and the untreated standard catalyst were tested for catalytic performance under test conditions that were designed to be more severe than described in Example 2. In this test, at operating conditions of 3 hr$^{-1}$ LHSV, 0.5 H$_2$/Hydrocarbon ratio and 140 psig, the catalysts were exposed to a hydrocarbon feed for 600 hours. Reactor temperatures were continually adjusted to maintain 84 wt. % aromatics in the $C_{5+}$ product as determined by an online gas chromatograph with flame ionization detection. As can be seen in FIG. 1, the treated Catalyst C had almost no activity loss during the test, but the untreated catalyst displayed a fouling rate that was quite high and the temperature required to maintain the targeted wt. % aromatics rose to 970° F. from 930° F. for the untreated catalyst, while the treated catalyst suffered no deactivation during the same period.

Additional Embodiments

The following enumerated embodiments are provided as non-limiting examples:
1. A method for removing tightly bound sodium from a zeolitic support comprising: contacting the support with a sodium specific removal agent to produce a treated support.
2. The method of embodiment 1 wherein the sodium specific removal agent comprises an ammonium-containing compound, an alkyl, aryl or arylalkyl ammonium containing compound, or combinations thereof
3. The method of embodiment 1 or 2 wherein the sodium specific removal agent comprises a tetraalkyl ammonium hydroxide.
4. The method of embodiment 3 wherein the tetraalkyl ammonium hydroxide comprises tetramethyl ammonium hydroxide, tetraethyl ammonium hydroxide, tetrapropyl ammonium hydroxide, tetraisopropyl ammonium hydroxide, tetrabutyl ammonium hydroxide, tetraisobutyl ammonium hydroxide, or combinations thereof.
5. The method of any preceding embodiment wherein the sodium specific removal agent is present in a solution at an amount of from about 0.01 wt. % to about 10 wt %.
6. The method of any preceding embodiment wherein the support is contacted with the sodium specific removal agent at a temperature range of from about 60° F. to about 200° F. for a time period of from about 0.1 hour to about 24 hours.
7. The method of any preceding embodiment further comprising contacting the treated support with a wash solution before said contacting, after said contacting, or both.
8. The method of embodiment 7 wherein the wash solution comprises a base.
9. The method of embodiment 8 wherein the base comprises potassium hydroxide, potassium acetate, potassium bromide, potassium hydroxide, potassium fluoride, potassium iodide, potassium t-butoxide, potassium ethoxide, or combinations thereof.
10. The method of any preceding embodiment further comprising:
    drying the treated support to form a dried treated support;
    calcining the dried treated support to form a catalyst support;
    contacting the catalyst support with a Group VIII metal and at least one halide to form a metalized halided support; and
    calcining the metalized halided support to form an aromatization catalyst.
11. The method of any preceding embodiment wherein the treated support has a sodium content of less than about 0.35 wt. %.
12. The method of embodiment 10 wherein the aromatization catalyst has a fouling rate of from about 0.01° F./hour to about 0.5° F./hour
13. A method comprising:
    providing a catalyst on a support that has been treated with a sodium specific removal agent to form a reduced sodium catalyst; and
    contacting the reduced sodium catalyst with a hydrocarbon feed in a reaction zone under conditions suitable for the production of an aromatic product.
14. The method of embodiment 13 wherein said aromatization catalyst prepared from the treated support has a reduced fouling rate when compared to an otherwise similar catalyst prepared from an untreated support.
15. The method of embodiments 13 or 14 wherein said aromatization catalyst prepared from the treated support has increased useful catalyst lifetime when compared to an otherwise similar catalyst prepared from an untreated support.

While embodiments of the disclosure have been shown and described, modifications thereof can be made by one skilled in the art without departing from the spirit and teachings of the disclosure. The embodiments described herein are exemplary only, and are not intended to be limiting. Many variations and modifications of the disclosure disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$, and an upper limit, $R_U$, is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method comprising:
   providing an aromatization catalyst comprising a treated support wherein the treated support is produced by contacting a zeolitic support with a sodium specific removal agent, wherein the zeolitic support comprises at least one zeolite selected from the group consisting of L-zeolite, X-zeolite, Y-zeolite, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, ZZA-26, SSZ-31, SSZ-33, SSZ-35, SSZ-37, SSZ-41, SSZ-42, SSZ-44, and MCM-58, and wherein the sodium specific removal agent comprises an ammonium-containing compound, an alkyl, aryl or arylalkyl ammonium-containing compound, or combinations thereof; and
   contacting the aromatization catalyst with a hydrocarbon feed in a reaction zone under conditions suitable for the production of an aromatic product.

2. The method of claim 1 wherein the aromatization catalyst has a fouling rate of from about 0.01° F./hour to about 0.5° F./hour as determined by a temperature needed to achieve a targeted conversion of the hydrocarbon feed to a selected wt. % aromatics in the aromatization product wherein the aromatization product comprises C5 and heavier hydrocarbons.

3. A method comprising:
   providing an aromatization catalyst comprising a treated support wherein the treated support is produced by contacting a zeolitic support with a sodium specific removal agent, wherein the zeolitic support comprises an L-zeolite, and wherein the sodium specific removal agent comprises an ammonium-containing compound, an alkyl, aryl or arylalkyl ammonium-containing compound, or combinations thereof; and
   contacting the aromatization catalyst with a hydrocarbon feed in a reaction zone under conditions suitable for the production of an aromatic product.

4. The method of claim 1 wherein the aromatization catalyst further comprises at least one halide.

5. The method of claim 1 wherein the aromatization catalyst further comprises a metal.

6. The method of claim 5 wherein the metal is selected from the group consisting of Group VIII metals of the Periodic Table of the Elements.

7. The method of claim 1 wherein the sodium specific removal agent further comprises a tetraalkyl ammonium hydroxide.

8. The method of claim 7 wherein the tetraalkyl ammonium hydroxide is selected from the group consisting of tetramethyl ammonium hydroxide, tetraethyl ammonium hydroxide, tetrapropyl ammonium hydroxide, tetraisopropyl ammonium hydroxide, tetrabutyl ammonium hydroxide, tetraisobutyl ammonium hydroxide, and combinations thereof.

9. The method of claim 1 further comprising washing the treated support with a wash solution at a temperature in the range of from about 70° F. to about 200° F. and drying the treated support to form a dried treated support subsequent to contacting the treated support with the sodium specific removal agent.

10. The method of claim 1 wherein the hydrocarbon feed comprises non-aromatic hydrocarbons containing at least six carbon atoms.

11. The method of claim 1 wherein the hydrocarbon feed comprises equal to or less than about 10 wt. % C5 and lighter hydrocarbons.

12. The method of claim 1 wherein the hydrocarbon feed comprises equal to less than about 10 wt. % C9 and heavier hydrocarbons.

13. The method of claim 1 wherein the hydrocarbon feed comprises naphtha.

14. The method of claim 13 wherein the naphtha is characterized by a boiling point of from about 70° F. to about 450° F.

15. The method of claim 1 wherein the hydrocarbon feed comprises saturated hydrocarbons, paraffinic hydrocarbons, olefinic hydrocarbons, acetylenic hydrocarbons, cyclic hydrocarbons, cyclic olefinic hydrocarbons, or combinations thereof.

16. The method of claim 1 wherein the hydrocarbon feed contains less than about 100 ppb sulfur.

17. The method of claim 1 further comprising purifying the hydrocarbon feed prior to contacting the hydrocarbon feed with the aromatization catalyst.

18. The method of claim 1 further comprising recovering the aromatic product and processing the recovered aromatic product to produce a compound selected from the group consisting of benzene, toluene, paraxylene, orthoxylene, metaxylene and combinations thereof.

* * * * *